US00PP27352P3

(12) United States Plant Patent
Olesen et al.

(10) Patent No.: US PP27,352 P3
(45) Date of Patent: Nov. 8, 2016

(54) ***CLEMATIS* PLANT NAMED 'EVIPO071'**

(50) Latin Name: *Clematis viticella*
Varietal Denomination: Evipo071

(71) Applicants: Mogens Nyegaard Olesen, Fredensborg (DK); Raymond J. Evison, St. Sampsons (GB)

(72) Inventors: Mogens Nyegaard Olesen, Fredensborg (DK); Raymond J. Evison, St. Sampsons (GB)

(73) Assignee: POULSEN ROSER A/S, Fredensborg (DK)

( * ) Notice: Subject to any disclaimer, the term of this patent is extended or adjusted under 35 U.S.C. 154(b) by 33 days.

(21) Appl. No.: 14/121,269

(22) Filed: Aug. 15, 2014

(65) Prior Publication Data

US 2016/0050825 P1 Feb. 18, 2016

(51) Int. Cl.
*A01H 5/02* (2006.01)

(52) U.S. Cl.
USPC ..... Plt./228

(58) Field of Classification Search
USPC ..... Plt./228
See application file for complete search history.

(56) References Cited

PUBLICATIONS

Retrieved from the Internet on Feb. 4, 2016—http://www.poulsenroser.com/assortment/clematiscollections/garland/marta.aspx 1/1).*
Perfection by Poulsen-*Clematis*—Main Varieties, 2013 (3 pgs totoal).*

* cited by examiner

*Primary Examiner* — Susan McCormick Ewoldt

(57) ABSTRACT

A new *Clematis* plant with a compact growth habit, profuse, light red flowers, and continuous summer flowering. The variety successfully propagates from softwood cuttings and is suitable for cultivation in commercial nursery culture. This new and distinct variety has shown to be uniform and stable in the resulting generations from asexual propagation from vegetative cuttings.

2 Drawing Sheets

Botanical classification: Genus: *Clematis*. Species: *viticella*.

Variety denomination: 'Evipo071'.

SUMMARY OF THE CLAIMED PLANT

The present invention constitutes a new and distinct variety of *Clematis* plant which originated from a controlled crossing between the female seed parent, an un-named seedling, and the male pollen parent, an un-named seedling. Both parent varieties are non-patented.

The two parents were crossed during the summer of 2002 and the resulting seeds were planted the following winter in a controlled environment in Guernsey, Channel Islands, United Kingdom. The new variety named 'Evipo071' originated as a single seedling from the stated cross.

The new *clematis* plant may be distinguished from its female seed parent and male pollen parent by the following characteristics. The seed parent has flowers which are red-purple while the new variety has light red flowers. The pollen parent tends to flower singly, while the new plant develops up to 7 flower buds per flowering branch.

The objective of the hybridization of this *clematis* plant was to create a new and distinct variety for nursery culture with unique qualities such as:

1. Uniform and abundant light red flowers;
2. Vigorous and compact growth, making the variety suitable for container culture; and
3. Improved disease resistance.

This combination of qualities was lacking in *clematis* plants that were in commercial cultivation and the qualities have been substantially achieved in the new variety.

'Evipo071' was selected by Mogens N. Olesen and Raymond J. Evison in their *clematis* development program in the Channel Islands, United Kingdom in 2003. Asexual reproduction of 'Evipo071' by means of vegetative cuttings and traditional layering was first performed by Mogens N. Olesen and Raymond J. Evison in the nursery during the summer of 2003. This initial and subsequent asexual propagations have demonstrated that the characteristics of 'Evipo071' are true to type and are transmitted from one generation to the next.

BRIEF DESCRIPTION OF THE DRAWING

The accompanying color illustrations show as true as is reasonably possible to obtain in color photographs of this type the typical characteristics of the buds, flowers, leaves, and stems, of 'Evipo071'.

Specifically illustrated in FIG. 1 are open flowers, tepals detached, a flowering branch with flower buds, reproductive flower parts detached, and seed heads.

DETAILED DESCRIPTION OF THE VARIETY

Figure 1:
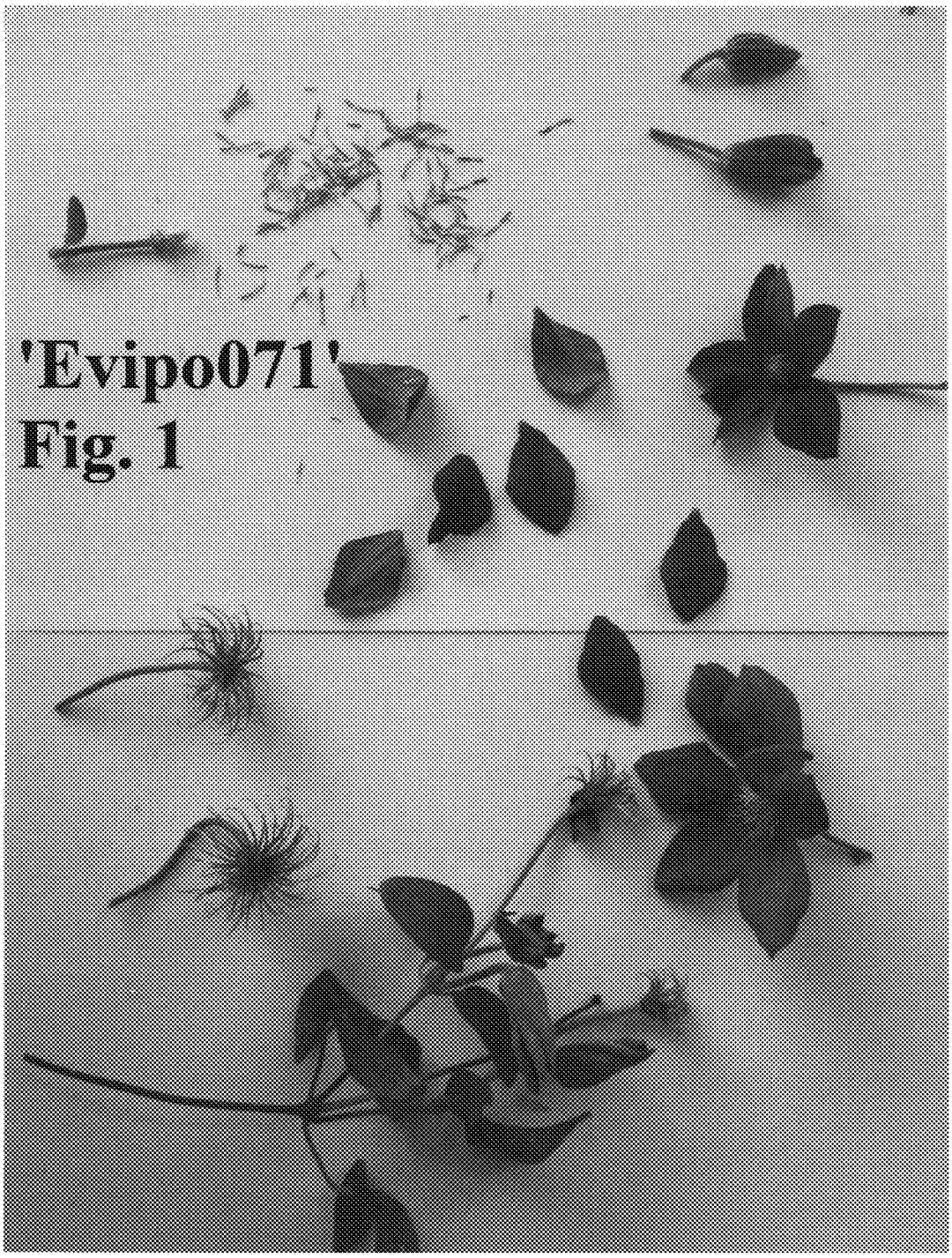
Figure 2:
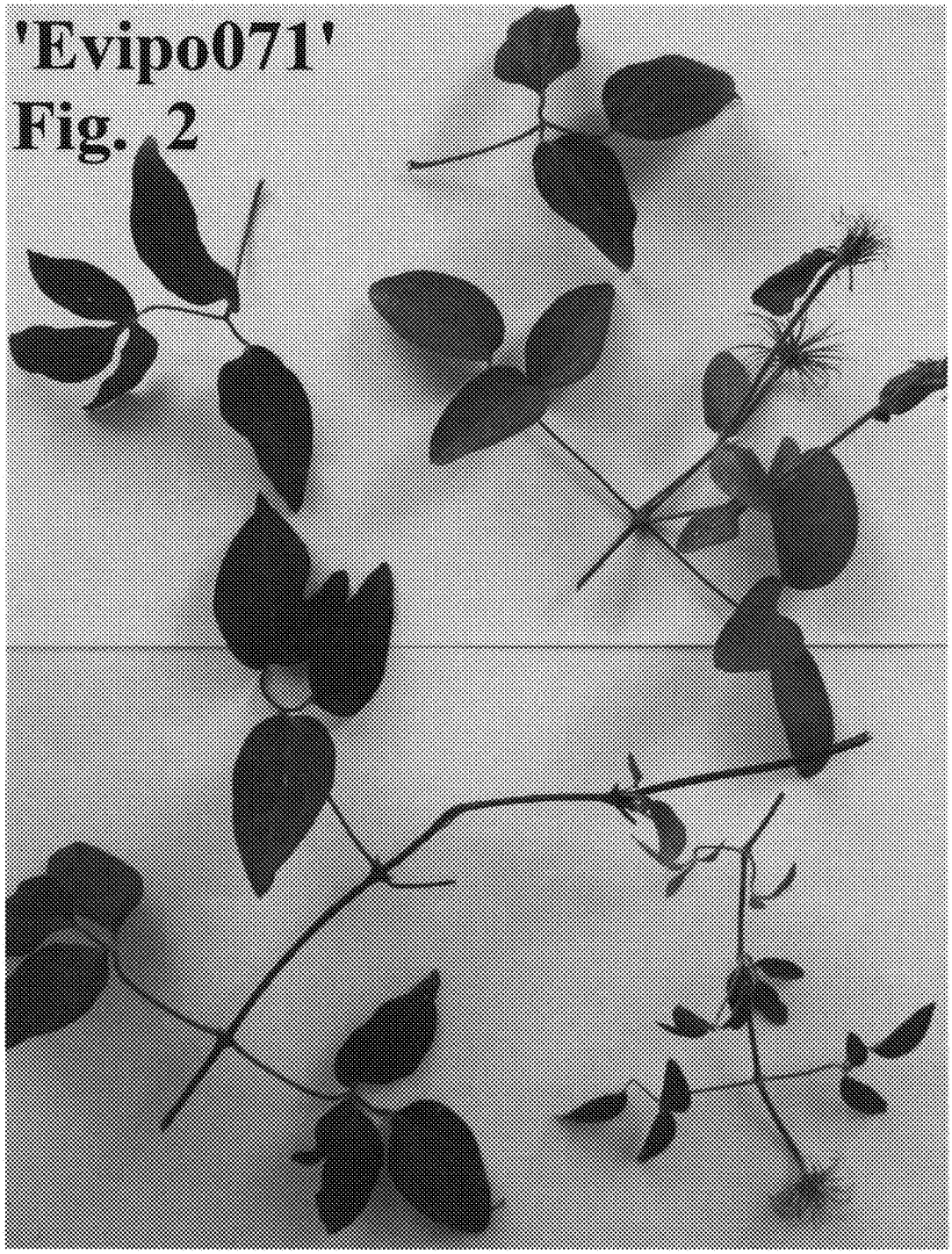
FIG. 2 shows juvenile and mature leaves and stems. Plants shown are 2 years of age.

The following is a detailed description of 'Evipo071', as observed in its growth throughout the flowering period in Fredensborg Denmark. Observed plants were cultivated for a period of 24 months in 2 liter containers. Certain phenotypical characteristics of the variety may vary under different environmental, cultural, agronomic, seasonal, and climatic conditions. Color references are made using The Royal Horticultural Society (London, England) Colour Chart, 2001, except where common terms of color are used.

For a comparison, several physical characteristics of the *clematis* variety 'Evipo016' described and illustrated in U.S. Plant Pat. No. 21,583 issued Dec. 21, 2010 are compared to 'Evipo071' in Chart 1.

CHART 1

| | 'Evipo071' | 'Evipo016' |
|---|---|---|
| Flower diameter | 65 to 80 mm | 130-185 mm |
| Tepal upper surface after opening | Red-Purple Group 59A | Red Group 53A |
| Anther colour | Greyed-Brown Group 199A | Grey Orange Group 177A |

Flower and Flower Bud

Blooming habit: Continuous. The natural flowering period is generally from April to September.

Flower bud:
- *Size.*—Normally 24 mm in length. Bud diameter is 10 mm.
- *Bud form.*—Elliptic.
- *Bud color.*—At ¼ opening flower buds are Purple Group 77B.

Peduncle:
- *Surface texture.*—Lightly pubescent.
- *Length.*—On average 25 mm.
- *Color.*—Yellow-Green Group 146B.
- *Strength.*—Moderately strong.

Receptacle:
- *Surface texture.*—Lightly pubescent.
- *Shape.*—Broad funnel.
- *Size.*—1 mm (h)×2 mm (w).
- *Color.*—Yellow-Green Group 146B.

Flower arrangement:
- *Location on vine.*—New growth only.
- *Borne.*—In clusters of up to 7 flowers in an umbel type inflorescence.
- *Flower attitude.*—Upwards, slightly horizontal.

Flower bloom:
- *Size.*—Flowers are 65 to 80 mm in diameter and 30 mm in depth.
- *Profile.*—Open flowers are convex.
- *Fragrance.*—None.
- *Lasting quality.*—Flowers normally remain up to 10 days on the plant.

Tepals:
- *Tepal color.*—Upon opening and after opening, the upper surface is Red-Purple Group 59A. The lower surface is Red-Purple Group 70A.
- *Quantity.*—Normally 6 to 7 tepals.
- *Size.*—30 to 45 mm in length by 20 mm wide.
- *Shape.*—Individual tepal shape is elliptic to lanceolate. The tepal apex is acuminate. The tepal base is typically acute.
- *Apex recurvature.*—Slightly curved.
- *Tepal cross section.*—Slightly reflexed.
- *Margins.*—Entire.
- *Persistence.*—Tepals drop off cleanly.
- *Overlap.*—Slightly.

Reproductive organs:
- *Arrangement.*—Moderately open.
- *Pollen.*—None observed.
- *Anthers.*—Size: 3 to 4 mm in length. Color: Greyed-Brown Group 199A. Quantity: On average, 80.
- *Filaments.*—Color: Red-Purple Group 67A at the base, becoming Red-Purple Group 68B towards the apex. Length: 4 to 7 mm.
- *Pistils.*—Quantity: On average, 60.
- *Stigmas.*—Superior in location relative to the length of the filaments and the height of the anthers.
- *Styles.*—Color: Green-Yellow Group 1C. Length: 8 to 10 mm.

Seed head characteristics:
- *Size.*—About 30 mm in height. 35 mm in diameter.
- *Quantity.*—The average number of seeds produced per seed head is 60.
- *Style appearance.*—Plumose, semi-erect.

Plant

Plant form: Climbing.

Plant growth: Vigorous.

Size: Seasons growth attains 200 to 300 cm in height. Average spread is 150 cm.

Stems:
- *Color.*—Juvenile stems are Yellow-Green Group 146A. Mature stems are Greyed-Orange Group 166A.
- *Internodes.*—40 to 70 cm between nodes.
- *Length.*—Normally 50 cm from the base of the plant to the flowering portion of the stem.
- *Diameter.*—2 to 3 mm.
- *Texture.*—Mature stems are ribbed.

Plant foliage:
- *Leaf characteristics.*—Deciduous.
- *Arrangement.*—Trifoliate.
- *Leaf size.*—Compound leaves are normally 90 to 110 mm (l)×85 to 120 mm (w). Leaflets are normally 40 to 50 mm (l)×25 to 30 mm (w).
- *Abundance.*—4 to 6 leaves per 10 cm of stem.
- *Leaf color.*—Juvenile upper Yellow-Green Group 144A. Juvenile lower Yellow-Green Group 146D. Mature upper Yellow-Green Group 147A. Mature lower Yellow-Green Group 147B.
- *Stipules.*—Absent.
- *Petioles.*—Size: 35 to 50 mm in length by 1 to 2 mm diameter. Texture: Smooth. Color: Yellow-Green Group 146A with some intonations of Brown Group 200B.
- *Petioloule.*—Size: 10 to 25 mm in length by 1 mm diameter. Texture: Smooth. Color: Yellow-Green Group 146A with some intonations of Brown Group 200B.
- *Leaflet shape.*—Generally elliptic. The base is rounded. The apex is acute.
- *Margin.*—Mostly entire. Some leaflets have a single oblique indentation.
- *Surface.*—The upper side is smooth. The lower side is somewhat rough.

*Thickness*.—Moderate.

*Glossiness*.—Not Glossy.

Disease resistance: Subject to any disease that normally attacks the species. However the variety is more tolerant to *clematis* wilt, *Ascochyta clematidina*, than some *clematis* known to the inventors.

Cold hardiness: The variety is tolerant to USDA Hardiness Zone 7.

Heat tolerance: The variety has been found to be suitable for climate conditions found in the American Horticulture Society heat zone 7.

We claim:

1. A new and distinct variety of *clematis* plant named 'Evipo071', substantially as described and illustrated, due to its abundant light red flowers with good keepability, attractive long lasting foliage and compact growth, year round flowering under glasshouse conditions, suitability for production from softwood cuttings in pots, durable flowers and foliage which make the variety suitable for distribution in the floral industry.

* * * * *

'Evipo071'

'Evipo071'